United States Patent
Mack

(10) Patent No.: US 7,216,873 B2
(45) Date of Patent: May 15, 2007

(54) DRILL CHUCK

(75) Inventor: Hans-Dieter Mack, Sontheim (DE)

(73) Assignee: Rohm GmbH, Sontheim (DE)

( * ) Notice: Subject to any disclaimer, the term of this patent is extended or adjusted under 35 U.S.C. 154(b) by 0 days.

(21) Appl. No.: 10/981,860

(22) Filed: Nov. 5, 2004

(65) Prior Publication Data
US 2005/0127617 A1 Jun. 16, 2005

(30) Foreign Application Priority Data
Nov. 6, 2003 (DE) ................ 103 52 311

(51) Int. Cl.
B23B 31/165 (2006.01)
(52) U.S. Cl. ............ 279/60; 279/64; 279/140; 403/348; 403/349
(58) Field of Classification Search ........ 279/60, 279/64, 140, 61, 62, 63, 95, 143; 403/348, 403/349, 361; 606/79, 80, 96
See application file for complete search history.

(56) References Cited

U.S. PATENT DOCUMENTS

| | | | | |
|---|---|---|---|---|
| 573,189 A * | 12/1896 | Vogel | ................ | 279/62 |
| 1,203,178 A * | 10/1916 | Bowers | ................ | 279/63 |
| 1,425,359 A * | 8/1922 | Barry | ................ | 81/53.2 |
| 2,544,088 A * | 3/1951 | Hollis | ................ | 279/60 |
| 3,506,277 A * | 4/1970 | Harms | ................ | 279/63 |
| 3,545,776 A * | 12/1970 | Haviland | ................ | 279/63 |
| 3,680,877 A * | 8/1972 | Happe | ................ | 279/62 |
| 3,702,705 A * | 11/1972 | Schadlich | ................ | 279/62 |
| 3,929,343 A * | 12/1975 | Wanner et al. | ................ | 279/81 |
| 3,970,323 A * | 7/1976 | Schnizler, Jr. | ................ | 279/64 |
| 4,213,623 A * | 7/1980 | Rohm | ................ | 279/140 |
| 4,230,327 A * | 10/1980 | Rohm | ................ | 279/61 |
| 4,527,809 A * | 7/1985 | Umbert | ................ | 279/64 |
| 4,661,009 A * | 4/1987 | Tripp | ................ | 403/349 |
| 4,753,142 A * | 6/1988 | Hornung | ................ | 81/429 |
| 4,799,832 A * | 1/1989 | Abbott | ................ | 408/123 |
| 4,842,288 A * | 6/1989 | Ando | ................ | 279/62 |
| 4,955,623 A * | 9/1990 | Rohm | ................ | 279/60 |
| 4,991,859 A * | 2/1991 | Rohm | ................ | 279/60 |
| 5,031,925 A * | 7/1991 | Tatsu et al. | ................ | 279/64 |
| 5,170,560 A * | 12/1992 | Allemann et al. | ................ | 30/228 |
| 5,378,002 A * | 1/1995 | Rohm | ................ | 279/62 |
| 5,390,940 A * | 2/1995 | Morlino et al. | ................ | 279/62 |
| 5,407,215 A * | 4/1995 | Yang | ................ | 279/64 |
| 5,522,606 A * | 6/1996 | Pressley et al. | ................ | 279/91 |
| 5,624,125 A * | 4/1997 | Rohm | ................ | 279/62 |
| 5,632,568 A * | 5/1997 | Fechter | ................ | 403/328 |

(Continued)

Primary Examiner—Monica Carter
Assistant Examiner—Michael W. Talbot
(74) Attorney, Agent, or Firm—Andrew Wilford

(57) ABSTRACT

A drill chuck has a chuck body centered on and axis, and a tightening element surrounding the body and rotatable thereon about the axis. The tightening element has a front sleeve formed with jaw-holding guides and a rear sleeve releasably coupled with the front sleeve. A retaining ring bears axially forward on the sleeve. Releasable locking formations on the ring and body are relatively displaceable between a retaining position preventing axial rearward shifting of the ring and sleeve on the body and a freeing position permitting such shifting. A pusher rotationally coupled to the jaws bears axially forward on the jaws. Interengaging screwthreads on the pusher and chuck body are provided so that relative rotation of the sleeve together with the jaws and pusher relative to the chuck body axially displaces the jaws between their positions.

13 Claims, 5 Drawing Sheets

U.S. PATENT DOCUMENTS

| | | | |
|---|---|---|---|
| 5,704,616 A * | 1/1998 | Huff et al. | 279/62 |
| 5,826,888 A * | 10/1998 | Weaver et al. | 279/23.1 |
| 5,918,886 A * | 7/1999 | Horiuchi et al. | 279/58 |
| 6,126,359 A * | 10/2000 | Dittrich et al. | 403/349 |
| 6,179,301 B1 * | 1/2001 | Steadings et al. | 279/62 |
| 6,505,840 B2 * | 1/2003 | Huggins et al. | 279/61 |
| 2003/0077136 A1 * | 4/2003 | Rohm | 408/239 R |
| 2005/0121861 A1 * | 6/2005 | Harris | 279/62 |

* cited by examiner

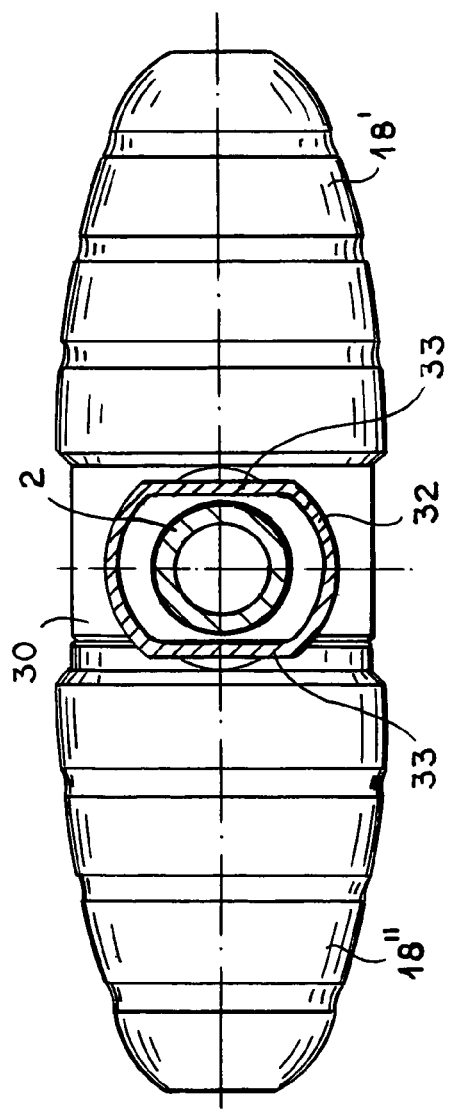
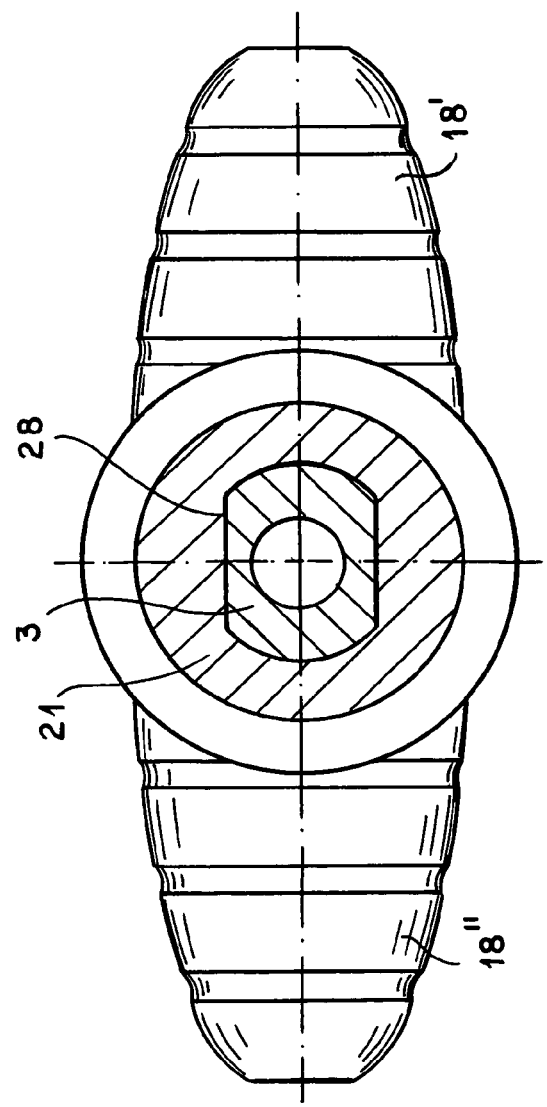

DRILL CHUCK

FIELD OF THE INVENTION

The present invention relates to a drill chuck. More particularly this invention concerns a hand-type drill chuck.

BACKGROUND OF THE INVENTION

A drill chuck is known that has a spindle extending along an axis, a chuck body fixed on the spindle and generally centered on the axis, and a tightening sleeve surrounding the body, rotatable thereon about the axis, and formed with a plurality of axially forwardly open angled guides spaced angularly about the axis. The sleeve cannot move axially relative to the body. A plurality of jaws angularly spaced about the axis are axially shiftable in the guides between a closely radially spaced and axially forward position and a widely radially spaced and axially rearward position. A pusher rotationally coupled to the jaws bears axially forward on the jaws, so that the sleeve, jaws, and pusher fit together for joint angular movement. Interengaging screwthreads couple the pusher to the chuck body so that relative rotation of the sleeve together with the jaws and pusher relative to the chuck body axially displaces the jaws between their positions. The user turns the sleeve in one direction on the chuck body to move the jaws together and grip a tool and in the opposite direction to move the jaws apart and release the tool.

Such a drill chuck is typically used in hand tools for drilling holes, driving screws, reaming, and the like. When used in a standard workshop some particles enter the chuck, which is designed as closed as possible to prevent this, but normally the minor amount of material than can enter the chuck is not a problem unless it builds up to the point of interfering with operation of the chuck mechanism.

When, however, such a chuck is used, for instance, in a bone drill for surgical/medical purposes, it is essential to be able to thoroughly clean and sterilize the chuck between uses, completely ridding of the tiniest particle. Thus it is necessary to be able to completely disassemble the chuck, clean and sterilize its parts, and reassemble it for each use. This is a time-consuming job that must normally be entrusted to a mechanically competent and trained person, greatly increasing the cost of using the equipment.

OBJECTS OF THE INVENTION

It is therefore an object of the present invention to provide an improved drill chuck.

Another object is the provision of such an improved drill chuck that overcomes the above-given disadvantages, in particular that can be taken completely apart and reassembled relatively easily.

SUMMARY OF THE INVENTION

A drill chuck has according to the invention a spindle extending along an axis, a chuck body fixed on the spindle and generally centered on the axis, and a tightening element surrounding the body and rotatable thereon about the axis. The tightening element has a front sleeve formed with a plurality of axially forwardly open angled guides spaced angularly about the axis, a rear sleeve, and means releasably axially and rotationally coupling the rear sleeve with the front sleeve. An axially forwardly directed formation on the sleeve and an axially rearwardly directed formation on the body prevent axial forward displacement of the sleeve relative to the body. A retaining ring bears axially forward on the sleeve. Releasable locking formations on the ring and on the body are relatively displaceable between a retaining position preventing axial rearward shifting of the ring and sleeve on the body and a freeing position permitting axial rearward shifting of the ring and sleeve on the body. A plurality of jaws angularly spaced about the axis are axially shiftable in the guides between a closely radially spaced axially forward position and a widely radially spaced axially rearward position. A pusher rotationally coupled to the jaws bears axially forward on the jaws. Interengaging screwthreads on the pusher and chuck body are provided so that relative rotation of the sleeve together with the jaws and pusher relative to the chuck body axially displaces the jaws between their positions.

Such a chuck can be easily and quickly disassembled, even by a person with no particular gift for mechanics. The entire chuck can be broken down into easily cleaned and sterilized elements, and can just as easily be reassembled after-ward.

According to the invention the axially forwardly directed formation on the sleeve is an axially forwardly directed annular shoulder centered on the axis and the axially rearwardly directed formation on the body is an axially rearwardly directed annular shoulder centered on the axis and confronting the axially forwardly directed shoulder of the sleeve. Such a construction is simple and very strong.

The latching formations in accordance with the invention include a radially outwardly projecting collar fixed axially relative to the spindle and body and of an outside shape not rotation symmetrical on the axis and a radially throughgoing hole in the retaining ring of a shape complementary to that of the spindle and fittable over the collar only in the freeing position. The ring is angularly displaceable on the body between the retaining and freeing positions. The shape is formed with at least one secantal flat. Thus a simple relative twisting of the spindle/chuck and the retaining ring allows the retaining ring to be aligned with the collar and pulled back over it, but normally the retaining ring is blocked by the collar against such axial rearward movement.

According to the invention a compression spring is braced axially between the retaining ring and the rear sleeve of the sleeve and presses the parts of the sleeve axially forward. This impedes unintentional actuation of the retaining ring, that is undesired turning of it into the freeing position.

The spindle and chuck body are unitarily formed with each other. This makes it easier to keep it clean and sterile for medical purposes.

The drill chuck further has according to the invention a handle releasable fixed to the spindle axially rearward of the chuck body. This handle is formed of two parts having interengaging threads and bearing diametrally oppositely on the spindle. The spindle has a region of noncylindrical, e.g. rectangular, shape engaged by the handle parts and one of the handle parts has a mouth of complementary noncylindrical shape. This handle can easily be mounted on the drill spindle for simple one-handed use of the drill.

The chuck body, pusher, and spindle are tubular according to the invention and form an axially throughgoing passage extending along and generally centered on the axis. This makes it possible to insert a long threaded rod or pin through the chuck and to use the chuck to set it in a predrilled hole.

To prevent loosening of the chuck, the rear sleeve part has a rear part fixed rotationally to the chuck body, a front part releasably axially and rotationally coupled to the front sleeve part, and a one-way coupling between the rear part and the front part displaceable between an engaged position only permitting rotation of the front part and front sleeve in a closing direction moving the jaws radially inward and a disengaged position permitting rotation of the front part and front sleeve in either angular direction relative to the rear part. A compression spring braced axially between the retaining ring and the rear part urges the one-way coupling into the engaged position. The one-way coupling is formed by interengageable saw teeth on the parts. Thus the rear part has to be pulled back against the spring force to open the one-way coupling and allow the jaws to be moved back.

The structure releasably axially and rotationally coupling the rear sleeve with the front sleeve can also include a bayonet coupling between the front sleeve and the rear sleeve. In another system this structure includes a clip circumferentially engaged around a joint between the rear sleeve and the front sleeve and having an inwardly directed coupling tooth engageable with the parts. Such a clip can easily be operated by hand, without tools.

BRIEF DESCRIPTION OF THE DRAWING

The above and other objects, features, and advantages will become more readily apparent from the following description, it being understood that any feature described with reference to one embodiment of the invention can be used where possible with any other embodiment and that reference numerals or letters not specifically mentioned with reference to one figure but identical to those of another refer to structure that is functionally if not structurally identical. In the accompanying drawing:

FIGS. 4, 5, and 6 are cross sections taken along respective lines IV—IV, V—V, and VI—VI of FIG. 1.

SPECIFIC DESCRIPTION

Figure 1:
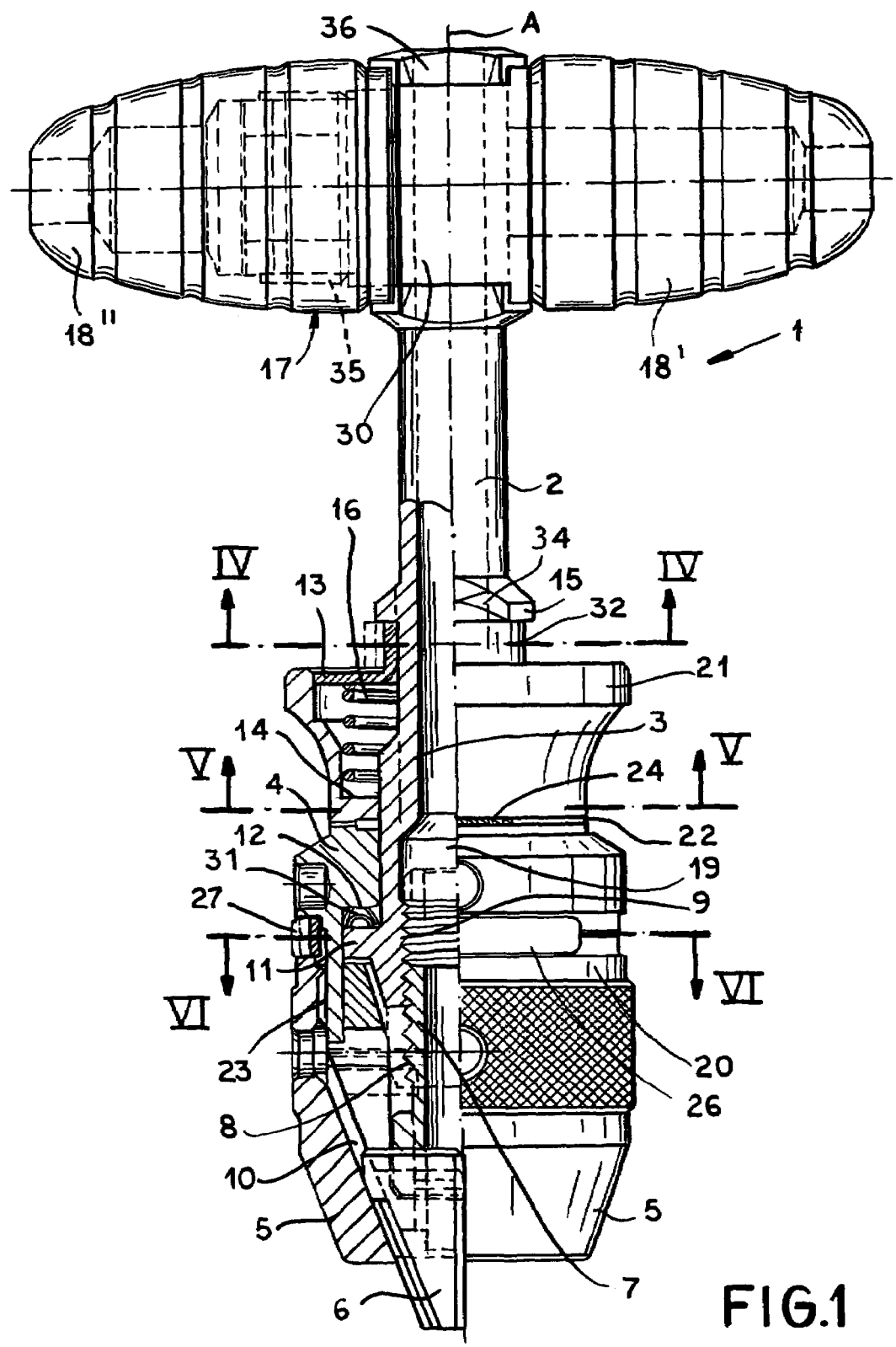
FIGS. 1, 2, and 3 are side views partly in axial section through chucks according to the invention.

As seen in FIGS. 1, 4, 5, and 6, a chuck 1 according to the invention has a cylindrically tubular spindle 2 centered on an axis A and here unitarily formed of steel with a chuck body 3 also centered on the axis A. The spindle 2 and body 3 form an axially throughgoing passage 19.

A tightening/loosening element that coaxially surrounds the body 3 is formed by a rear sleeve 4 having a front part 20 and a rear part 21 and by a front sleeve 5. The front sleeve 5 is normally axially and angularly coupled to the rear sleeve 4 as described below and is formed with a plurality (here three) of guides 10 each formed as a radially inwardly open square-section groove extending in a plane including the axis A but each with a floor extending at a small acute angle to the axis A. Each guide 10 holds a respective right-triangular steel jaw 6 that can move between the illustrated radially inward and axially forward position and an unillustrated radially outward and axially rearward position.

A tubular steel pusher 7 bears axially forward on and is rotationally coupled to the jaws 6 and through the jaws 6 to the front sleeve 5 and to the front part 20 of the rear sleeve 4, to which end the pusher 7 is formed with axially forwardly open notches fitting over rear ends of the jaws 6. Interengaging screwthreads 8 and 9 on the pusher 7 and on the chuck body 3 axially shift the pusher 7 and jaws 6 axially forward when the sleeve 5 and sleeve part 20 are rotated with the jaws 6 in one angular direction and axially backward when rotated in the opposite direction.

The chuck body 3 is formed with a radially outwardly projecting ridge 11 forming a rearwardly directed annular and planar shoulder against which bears an axially forwardly directed complementary shoulder formed on a radially inwardly projecting ridge 12 of the rear sleeve 4. A row of balls 31 ride on the confronting shoulders to ensure smooth relative rotation of the sleeves 4 and 5 on the body 3.

A retaining disk or ring 13 bears axially forward on the rear end of a coil compression spring 16 bearing axially rearward via the ring 13 on a collar 15 of the body 3 and axially forward on a rearwardly directed shoulder 14 of the ridge 12 of the rear sleeve 4 so as to press the sleeves 4 and 5 axially forward. This ring 13 axially rearwardly closes the rear sleeve 4 and has a rearwardly projecting collar 32 of cylindrical shape with two opposite secantal flats 33 (FIG. 4) extending in planes parallel to each other and symmetrically flanking the axis A. The spindle 2 and/or body 3 is formed rearward of the ring 13 with the radially outwardly projecting collar 15 having a pair of secantal flats 34 like the flats 33. When the flats 33 are axially aligned in a freeing position with the flats 34, the ring 13 can move axially rearward of the collar 15, but, when they are misaligned in a retaining position, the ring 13 is blocked against axial movement rearward of the collar 15.

A handle 17 has a pair of arms 18' and 18" that diametrically embrace the rear end of the spindle 2, extending radially oppositely from it. The spindle 2 has a square-section rear end 36 and the arm 18' has a pair of arms 30 that form a rectangular notch that in turn fits complementarily over this rear end 36. In addition the arms 30 are formed with screwthreads 35 that releasably couple the arm 18' to the other arm 18". Thus the handle 17 can be easily installed on and removed from the spindle 2 simply by screwing and unscrewing the arm 18".

The rear-sleeve front part 20 and rear part 21 bear on each other axially at a joint 22 where they are formed with complementary annular arrays of sawteeth 24 forming a one-way coupling. The rear part 21 and the body 3 are formed with complementary flats 28 (see FIG. 5) that rotationally lock the rear part 21 on the body 3 while permitting it to move axially. So long as the spring 16 is pressing the two parts 20 and 21 together at 22, the arrays of teeth 24 are in mesh and the front part 20 can only rotate on the body 3 about the axis A in a direction moving the jaws 6 radially together, opposite rotation being blocked. When the rear part 21 is pulled back against the spring force to disengage the teeth 24, the front part 21 and jaws 6 can be rotated in either direction. Thus the chuck 1 can only be tightened and is actually prevented from loosening unless the rear part 21 is intentionally pulled back off the front part 20.

The front part 20 of the rear sleeve 4 and the front sleeve 5 are normally locked together. This is effected by inner and outer screwthreads 23 on the sleeve 5 and part 20, and by a spring clip 26 having a tooth 27 engaging in a pair of axially confronting notches 29 of the part 20 and sleeve 5. Thus when this tooth 27 of the clip 26 engages in the notches 29, it rotationally couples the part 20 and sleeve 5. This clip 26 can easily be pulled manually without the use of tools off the chuck 1, thereby allowing the front sleeve 5 to be rotated relative to the part 20 and separating them at the screwthread 23.

A tool is gripped by the jaws 6 of the chuck 1 by fitting the tool, e.g. a drill bit, between the jaws 6 and rotating the front sleeve 5 and front part 20 in the direction moving the jaws 6 together, such movement being permitted by the one-way coupling teeth 24. To dechuck this tool, the rear part 21 is pulled back to disengage the teeth 24 and allow the front sleeve 5 and front part 20 to be reverse rotated.

To clean and sterilize the elements of the chuck 1, the handle 17 is disassembled by unscrewing the arm 18″ and pulling the arm 18′ off the stem 2. Then the clip 26 is removed to decouple the front sleeve 5 from the front part 20 and the front sleeve 5 is screwed with the jaws 6 off the front part 20. Normally only this much disassembly is used as only the front-end parts of the chuck 1 need careful cleaning.

To completely disassemble the chuck 1, the ring 13 is arrested and the spindle 2 and body 3 are turned to align the flats 33 of the collar 32 with the flats 34 so that the ring 13 can be moved back past the rim 15. This exposes the spring 16 and allows all the internal parts of the chuck 1 to be accessed, cleaned, and sterilized.

Such disassembly, and the following reassembly which takes place in the opposite order, can be done completely without the use of tools. Furthermore the chuck parts are all fairly simple and only fit together one way, so that a reasonably attentive person who performs the disassembly can easily reassemble the device.

Figure 2:
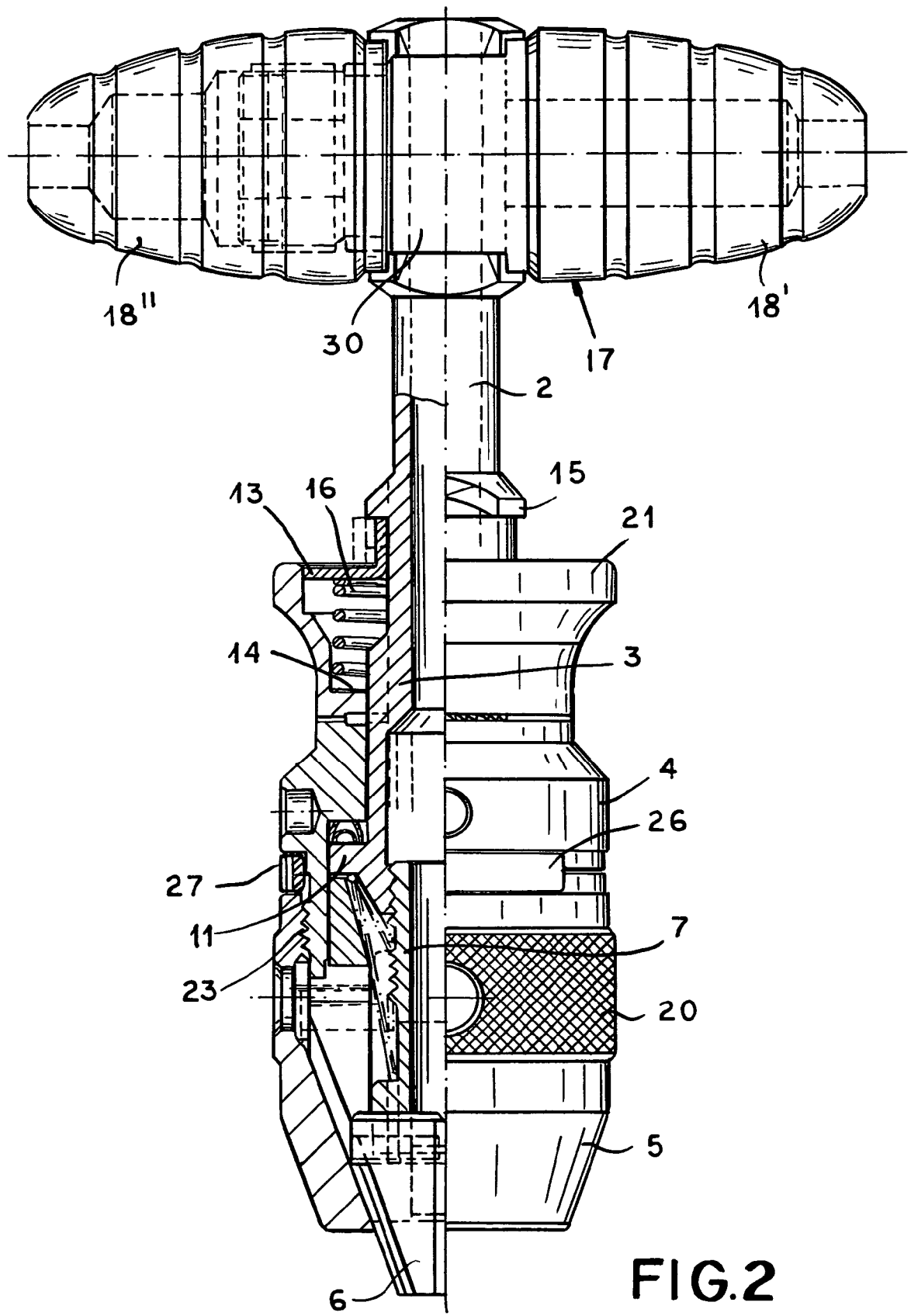

FIG. 2 shows an embodiment substantially identical to that of FIGS. 1, 4, 5, and 6, but with different proportions.

Figure 3:
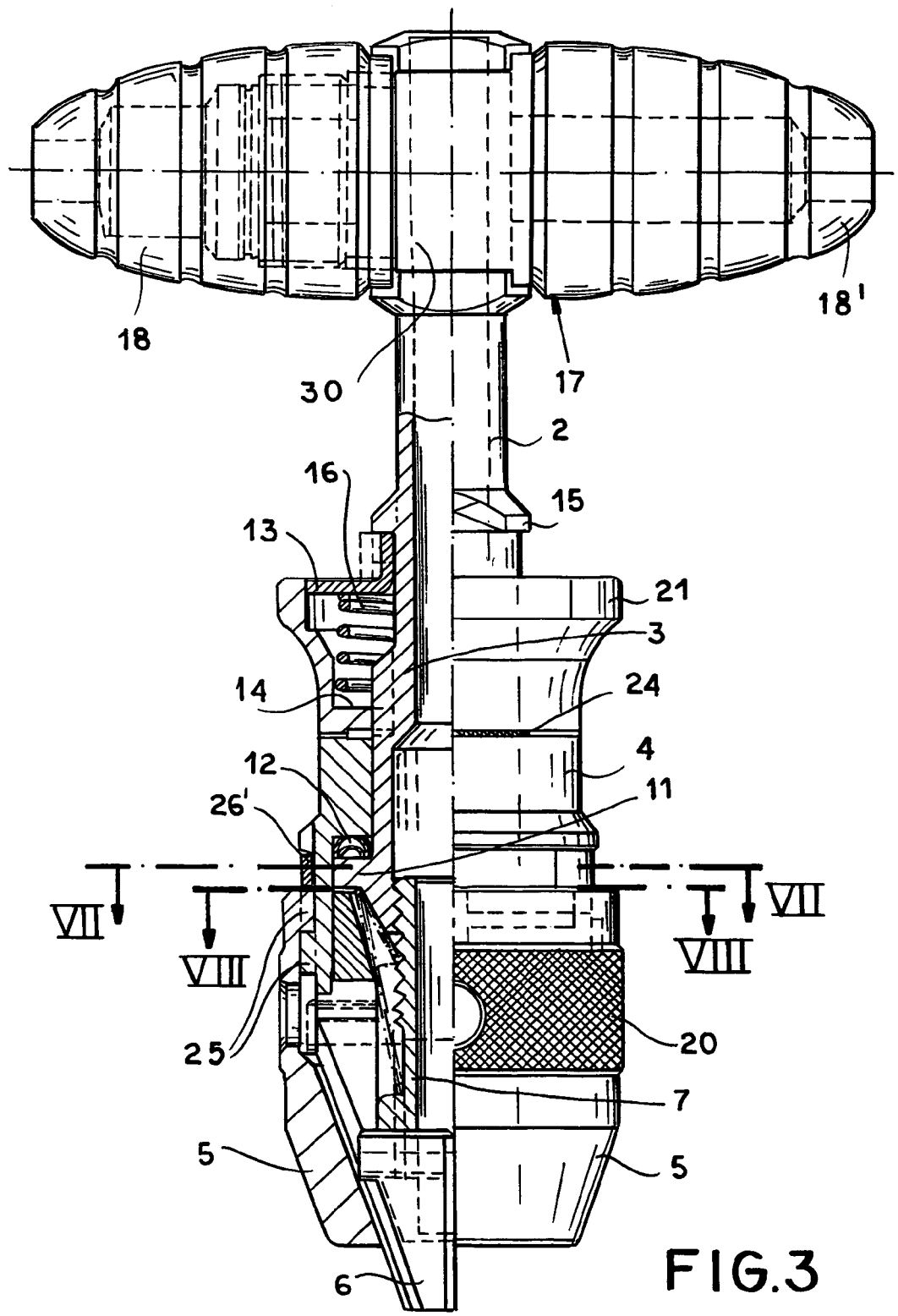
Figure 6:
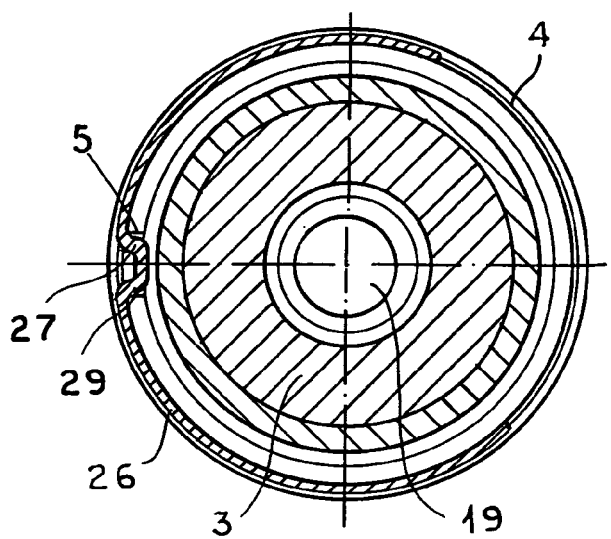
Figure 7:
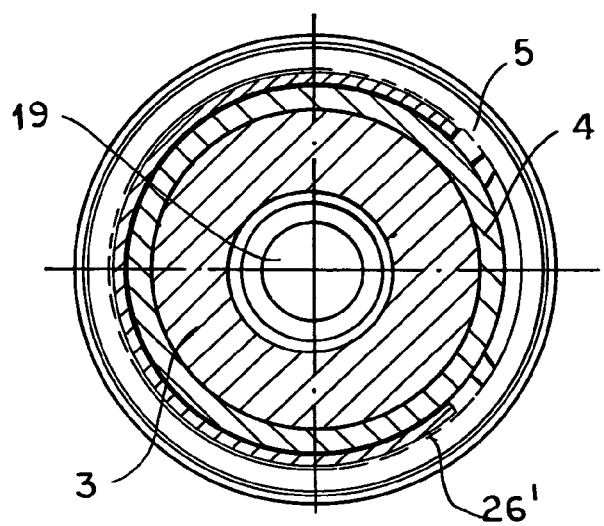
FIGS. 7 and 8 are cross sections taken along respective lines VII—VII and VIII—VIII of FIG. 3.
Figure 8:
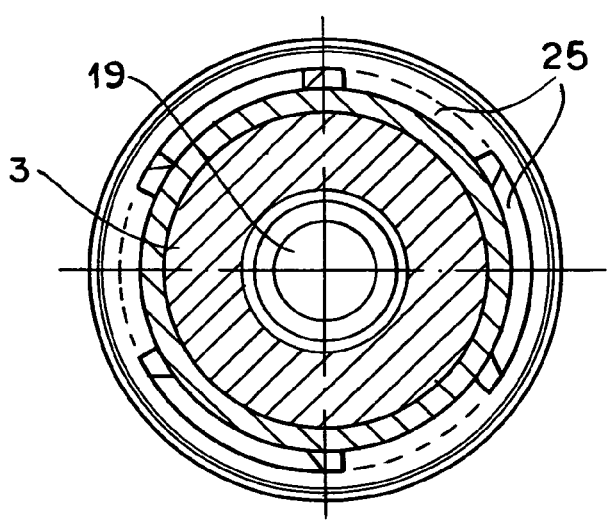

FIGS. 3, 7, and 8 show an arrangement where the front part 20 of the rear sleeve 4 fits at a bayonet coupling 25 with the front sleeve 5. A clip 26′ must be removed to allow the bayonet coupling 25 to be actuated to separate the part 20 from the sleeve 5.

I claim:

1. A drill chuck comprising:
    a spindle extending along an axis;
    a chuck body unitarily formed with the spindle and generally centered on the axis;
    a transversely projecting handle releasably fixed to the spindle axially rearward of the chuck body;
    a tightening element surrounding the body, rotatable thereon about the axis, and having
        a front sleeve formed with a plurality of axially forwardly open angled guides spaced angularly about the axis,
        a rear sleeve, and
        means releasably axially and rotationally coupling the rear sleeve with the front sleeve;
    means including an axially forwardly directed formation on one of the sleeves and an axially rearwardly directed formation on the body for preventing axial forward displacement of the rear sleeve relative to the body;
    a retaining ring bearing axially forward on the rear sleeve;
    means including releasable locking formations on the ring and on the body relatively angularly displaceable between a retaining position bearing axially on each other for preventing axial rearward shifting of the ring and rear sleeve on the body and a freeing position slidable axially past each other for permitting axial rearward shifting of the ring and rear sleeve on the body;
    a plurality of jaws angularly spaced about the axis and axially shiftable in the guides between a closely radially spaced axially forward position and a widely radially spaced axially rearward position;
    a pusher rotationally coupled to the jaws and bearing axially forward on the jaws, the chuck body, pusher, and spindle being tubular and forming an axially throughgoing and open passage extending along and generally centered on the axis;
    interengaging screwthreads on the pusher and chuck body, whereby relative rotation of the front sleeve together with the jaws and pusher relative to the chuck body axially displaces the jaws between their positions.

2. The drill chuck defined in claim 1 wherein the axially forwardly directed formation on the sleeve is an axially forwardly directed annular shoulder centered on the axis and the axially rearwardly directed formation on the body is an axially rearwardly directed annular shoulder centered on the axis and confronting the axially forwardly directed shoulder of the sleeve.

3. The drill chuck defined in claim 1 wherein the latching formations include
    a radially outwardly projecting collar fixed axially relative to the spindle and body and of an outside shape not rotation symmetrical on the axis, and
    a radially throughgoing hole in the retaining ring of a shape complementary to that of the spindle and fittable over the collar only in the freeing position, the ring being angularly displaceable on the body between the retaining and freeing positions.

4. The drill chuck defined in claim 3 wherein the shape is formed with at least one secantal flat.

5. The drill chuck defined in claim 1, further comprising a compression spring braced axially between the retaining ring and the rear sleeve and pressing the front and rear sleeves axially forward.

6. The drill chuck defined in claim 1 wherein the handle is formed of two parts having interengaging threads and bearing diametrally oppositely on the spindle.

7. The drill chuck defined in claim 6 wherein the spindle has a region of noncylindrical shape engaged by the handle parts and one of the handle parts has a mouth of complementary noncylindrical shape.

8. The drill chuck defined in claim 7 wherein the shape is rectangular.

9. The drill chuck defined in claim 1 wherein the rear sleeve part has
    a rear part fixed rotationally to the chuck body;
    a front part releasably axially and rotationally coupled to the front sleeve part; and
    means including a one-way coupling between the rear part and the front part displaceable between an engaged position only permitting rotation of the front part and front sleeve in a closing direction moving the jaws radially inward and a disengaged position permitting rotation of the front part and front sleeve in either angular direction relative to the rear part.

10. The drill chuck defined in claim 9, further comprising a compression spring braced axially between the retaining ring and the rear part and urging the one-way coupling into the engaged position.

11. The drill chuck defined in claim 9 wherein the one-way coupling is formed by interengageable saw teeth on the parts.

12. The drill chuck defined in claim 1 wherein the means releasably axially and rotationally coupling the rear sleeve with the front sleeve includes a bayonet coupling between the front sleeve and the front sleeve.

13. The drill chuck defined in claim 1 wherein the means releasably axially and rotationally coupling the rear sleeve with the front sleeve includes a clip circumferentially engaged around a joint between the rear sleeve and the front sleeve and having an inwardly directed coupling tooth engageable with the front and rear sleeves.

* * * * *